(12) United States Patent
Lecuivre et al.

(10) Patent No.: US 9,439,749 B2
(45) Date of Patent: Sep. 13, 2016

(54) KNIT WITH ZONES WITHOUT BARBS, METHOD OF MAKING SAME AND PROSTHESES OBTAINED THEREFROM

(71) Applicant: Sofradim Production, Trévoux (FR)

(72) Inventors: Julie Lecuivre, Jassans-Riottier (FR); Pierre Bailly, Caluire-et-Cuire (FR)

(73) Assignee: Sofradim Production, Trevoux (FR)

( * ) Notice: Subject to any disclaimer, the term of this patent is extended or adjusted under 35 U.S.C. 154(b) by 164 days.

(21) Appl. No.: 14/366,363

(22) PCT Filed: Dec. 27, 2012

(86) PCT No.: PCT/EP2012/076979
§ 371 (c)(1),
(2) Date: Jun. 18, 2014

(87) PCT Pub. No.: WO2013/098345
PCT Pub. Date: Jul. 4, 2013

(65) Prior Publication Data
US 2014/0350577 A1     Nov. 27, 2014

(30) Foreign Application Priority Data

Dec. 29, 2011   (FR) ...................................... 11 62532

(51) Int. Cl.
*A61F 2/02*     (2006.01)
*A61F 2/00*     (2006.01)
(Continued)

(52) U.S. Cl.
CPC .............. *A61F 2/0063* (2013.01); *D04B 21/12* (2013.01); *D04B 21/20* (2013.01); *D06C 7/00* (2013.01);
(Continued)

(58) Field of Classification Search
CPC ..................... A61F 2/0063; A61F 2002/0068; D06C 7/00; D04B 21/20; D04B 21/12; D10B 2403/0111; D10B 2401/12; D10B 2509/08; D10B 2501/0632
See application file for complete search history.

(56) References Cited

U.S. PATENT DOCUMENTS 4,454,183 A * 6/1984 Wollman ........... A44B 18/0042
                                                                    24/306
4,770,917 A * 9/1988 Tochacek ........... A44B 18/0003
                                                                    156/72
(Continued)

FOREIGN PATENT DOCUMENTS

CN      101883538 A      11/2010
DE      102009015302 A1   9/2010
(Continued)

OTHER PUBLICATIONS

Chinese Office Action, Application No. 201280065605.8 dated Apr. 17, 2015.
(Continued)

*Primary Examiner* — Julian W Woo

(57) ABSTRACT

The present invention relates to an openwork prosthetic knit (1) made from a single piece based on first yarns of biocompatible polymer materials that define a first face (2) and a second face that are opposite one another and on a second biocompatible yarn that generates barbs (3) that protrude outwards from at least said first face, characterized in that said first face comprises at least one zone in which it is provided with said barbs and at least one zone (5) in which it is free of such barbs. It also relates to a process for manufacturing such a knit (1) and to a prosthesis comprising such a knit (1).

20 Claims, 1 Drawing Sheet

(51) Int. Cl.
*D04B 21/12* (2006.01)
*D04B 21/20* (2006.01)
*D06C 7/00* (2006.01)

(52) U.S. Cl.
CPC .... *A61F 2002/0068* (2013.01); *D10B 2401/12* (2013.01); *D10B 2403/0111* (2013.01); *D10B 2501/0632* (2013.01); *D10B 2509/08* (2013.01)

(56) References Cited

U.S. PATENT DOCUMENTS

| | | | | |
|---|---|---|---|---|
| 6,971,252 | B2* | 12/2005 | Therin | A61F 2/0045 66/170 |
| 7,905,825 | B2* | 3/2011 | Arnal | A61B 17/06066 600/30 |
| 8,418,508 | B2* | 4/2013 | Lecuivre | A61F 2/0063 66/170 |
| 8,834,578 | B2* | 9/2014 | Bayon | A61L 27/38 623/23.75 |
| 2009/0192532 | A1* | 7/2009 | Spinnler | A61F 2/0063 606/153 |
| 2013/0172915 | A1* | 7/2013 | Thomas | A61B 17/06166 606/151 |

FOREIGN PATENT DOCUMENTS

| | | |
|---|---|---|
| EP | 2 229 918 A1 | 9/2010 |
| FR | 2 924 330 A1 | 6/2009 |
| FR | 2 935 605 A1 | 3/2010 |
| WO | WO 01/81667 A1 | 11/2001 |

OTHER PUBLICATIONS

International Search Report for PCT/EP12/076979 date of completion is Apr. 17, 2013 (3 pages).

CN Office Action issued Dec. 31, 2015 in CN Patent Application No. 201280065605.8, together with English language translation, 19 pages.

* cited by examiner

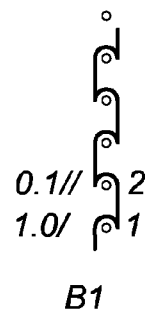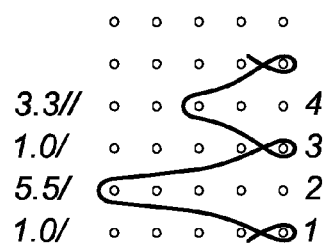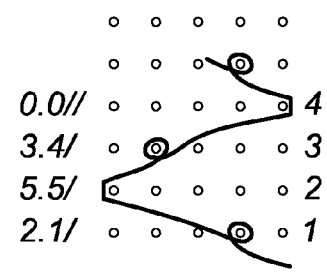
Fig. 1A  Fig. 1B  Fig. 1C
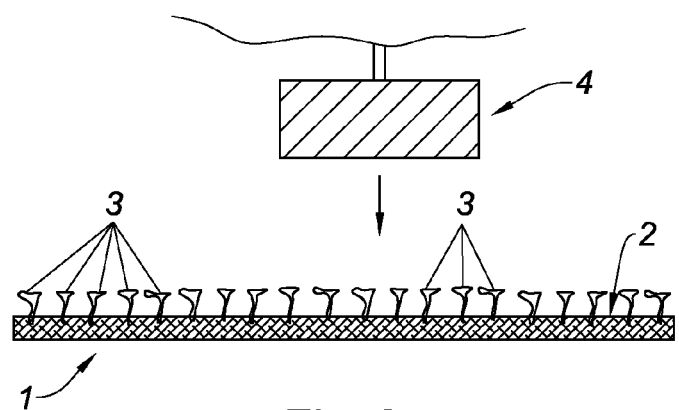
Fig. 2
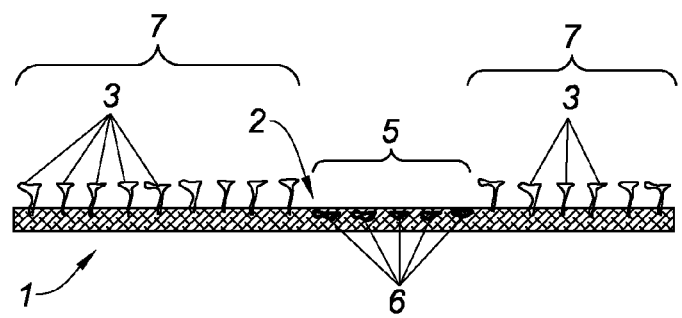
Fig. 3

KNIT WITH ZONES WITHOUT BARBS, METHOD OF MAKING SAME AND PROSTHESES OBTAINED THEREFROM

CROSS-REFERENCE TO RELATED APPLICATIONS

This application is a National Stage Application of PCT/EP12/076979 under 35 USC §371 (a), which claims priority of French Patent Application Serial No. 11/62532 filed Dec. 29, 2011, the disclosures of each of the above-identified applications are hereby incorporated by reference in their entirety.

The present invention relates to a prosthetic knit made from a single piece, at least one face of which comprises one or more zones provided with barbs and one or more zones free of barbs. Such a knit can particularly be used for producing prostheses requiring variable fastening capabilities, for example for fastening to biological tissues, on the surface of said prosthesis.

Wall reinforcement prostheses, for example for the abdominal wall, are widely used in surgery. These prostheses are intended to treat hernias by temporarily or permanently filling a tissue defect. These prostheses are generally made of biocompatible prosthetic fabric and can have a number of shapes, for example rectangular, circular or oval, depending on the anatomical structure to which they are to be fitted. Some of these prostheses are made from entirely bioresorbable yarns and are intended to disappear after having performed their reinforcing role while cell colonization takes place and tissue rehabilitation takes over. Others comprise non-bioresorbable yarns and are intended to remain permanently in the body of the patient.

Some of these prostheses are made from an arrangement of yarns, a knit, a woven or non-woven fabric, comprising barbs protruding outwards from one face of the prosthesis: these barbs constitute hooks that are able to fix themselves either in another prosthetic fabric, belonging to the same prosthesis or not, or directly in the biological tissues, for example the abdominal wall.

The presence of barbs capable of fastening directly to biological tissues makes it possible to do away with additional means of attachment for the prosthesis, such as staples, sutures, etc. However, in certain cases, for example when the prosthesis must be implanted in the vicinity of fragile or sensitive organs, such as vessels, nerves, or else the spermatic cord, it may prove advantageous for the part of the prosthesis in contact with these organs to be free of such barbs.

In such cases, a composite prosthesis is generally produced comprising a first textile portion with barbs and a second textile portion without barbs that is assembled to the first portion, for example by means of stitching, or ultrasonic welding, etc. Such a process is tedious and complicated. Furthermore, due to the discontinuous nature of the textile making up the composite prosthesis thus obtained, the mechanical properties of the prosthesis are not the same over the whole of the prosthesis. In particular, the assembly zone of the first textile portion to the second textile portion generally constitutes a line of weakness of the prosthesis.

Therefore, there remains a need for a knit that makes it possible to provide a reinforcing prosthesis both with zones that have good fastening capabilities and smoother and non-traumatizing zones, and which would not require additional steps during its manufacturing process.

The present invention aims to meet this need by proposing a knit made of a single piece, at least one face of which has one or more fastening zones and one or more zones without fastenings.

The present invention relates to an openwork prosthetic knit made from a single piece based on at least a first yarn made of biocompatible polymer material that defines a first face and a second face that are opposite one another and on a second biocompatible yarn that generates barbs that protrude outwards from at least said first face, characterized in that said first face comprises at least one zone in which it is provided with said barbs and at least one zone in which it is free of such barbs.

The present invention also relates to a process for manufacturing a knit such as above comprising the following steps:
 a) manufacture of an arrangement of at least one first yarn of biocompatible polymer material that defines a first face and a second face that are opposite one another for said knit and of at least one second yarn, namely a biocompatible heat-fusible monofilament yarn, that forms small loops that protrude outwards from said first face, by knitting on a warp or Raschel knitting machine of said first yarn(s) and second yarns using at least three guide bars, said first yarn(s) being threaded, continuously on two of said three guide bars, and said second yarn being threaded continuously on the third guide bar,
 b) cutting, by melting, of said loops, each loop generating two barbs,
 c) melting and flattening said barbs over one or more given zone(s) of the first face by application, with pressure, to said zone(s) of an anvil heated to the melting point of said barbs.

In the present application, the expression "prosthetic knit" is understood to mean a knit intended to be implanted in the human or animal body in the form of a prosthesis or of any other part made at least partly with said knit.

In the present application, the expression "openwork knit" is understood to mean a knit having a weave or weaves that determine cells or voids in the thickness of the knit and on the faces of the knit, these cells or voids possibly forming channels that open on both sides of the knit. Such an openwork knit enables better tissue integration.

The expression "knit made from a single piece" is understood according to the present application to mean that the knit is produced in a single knitting step and does not comprise additional textile added by any means of attachment such as stitching, ultrasonic welding, etc. Thus, the knit according to the invention has mechanical properties that are constant over the whole of its surface, independently of the zones with or without barbs.

The first yarns of the knit according to the invention may be monofilament and/or multifilament yarns, and may be made from any biodegradable or non-biodegradable biocompatible material. Thus, the biodegradable materials suitable for the first yarns of the knit of the present invention may be selected from polylactic acid (PLA), polyglycolic acid (PGA), oxidized cellulose, polycaprolactone (PCL), polydioxanone (PDO), trimethylene carbonate (TMC), polyvinyl alcohol (PVA), polyhydroxyalkanoates (PHAs), copolymers thereof and mixtures thereof. The non-biodegradable materials suitable for the first yarns of the knit of the present invention may be selected from polyethylene terephthalate (PET), polyamides, aramids, expanded polytetrafluoroethylene, polyurethane, polyvinylidene difluoride (PVDF), butyl ester polymers, polyetheretherketone (PEEK), polyolefins (such as polyethylene or polypropylene), polyethers, copper alloys, silver or platinum alloys, medical grades of steel such as medical-grade stainless steel, and combinations thereof.

In one embodiment of the invention, said first face comprises several of said zones provided with said barbs, and several of said zones which are free of such barbs.

In the zone(s) where they are present, the barbs of the knit according to the invention may protrude from the first face substantially perpendicular to the plane of said face or alternatively along one or more planes that are inclined relative to the plane of said face. Generally, these barbs have the shape of a shaft, having the diameter of the yarn used for their formation, surmounted by a head having a diameter greater than that of the shaft.

For example, the first face of the knit according to the invention may comprise several zones free of barbs, these zones being intended to be located opposite fragile or sensitive organs once the prosthesis or knit is implanted, the remainder of the first face of the knit being provided with barbs located opposite other organs, for example muscles, to which they will be able to fasten in order to attach the knit or the prosthesis.

Alternatively, these barbs may be intended to be entangled in one or more arrangements of yarns, fibres, filaments and/or multifilaments of another prosthetic textile, for example in order to form a composite reinforcing prosthesis, in particular if it is desired, for example, for only certain zones of the knit according to the invention to fasten in this other prosthetic textile.

Thus, it is possible to prepare knits having a zone free of barbs, the remainder of the knit being provided with barbs. It is for example possible to place the barb-free zone opposite a nerve or a fragile organ, the remainder of the knit being capable of fastening to muscles for example. Such a knit is particularly useful for manufacturing a prosthesis for repairing inguinal hernias for example.

In one embodiment, the second yarn, namely that yarn which generates the barbs, is a heat-fusible monofilament yarn. Thus, the step of manufacturing the barbs is facilitated, as will become apparent from the description that follows.

In one embodiment of the invention said first yarns have a melting point strictly above that of said second yarn. Thus, the step of manufacturing the barb-free zone or zones is greatly facilitated.

For example, said second yarn is a monofilament yarn made of polylactic acid and said first yarns are monofilament yarns made of polyethylene terephthalate (PET). In such an embodiment, the melting point of polylactic acid being 185° C., and the melting point of polyethylene terephthalate (PET) being 258° C., a value above 185° C., the anvil intended for forming the barb-free zone is heated to around 185° C. Thus, when the anvil heated to 185° C. is applied to the knit in order to form a barb-free zone, only the barbs melt; the first yarns, made of polyethylene terephthalate (PET), which form the ground of the knit, are not damaged by the application of the anvil. The ground structure of the knit is not therefore modified and the ground of the knit therefore retains its integrity and its mechanical properties. Furthermore, since the anvil is applied to the barbs with a certain pressure, for example 100 N, the barbs not only melt, but are also flattened and no longer protrude outwards from the first face. A barb-free zone, which is smooth and non-traumatizing, is thus obtained.

In one embodiment of the invention, the chart followed for the knitting of said first and second yarns is selected from the following charts:

for said first yarns, threaded on two guide bars B1 and B2, according to the ISO 11676 standard:
bar B1: 1.0/0.1/
bar B2: 1.0/5.5/1.0/3.3/ or 1.0/7.7/6.6/7.7/
for said second yarn, threaded on the third guide bar B3, according to the ISO 11676 standard:
bar B3: 2.1/5.5/3.4/0.0/

Such embodiments make it possible to obtain openings on both faces of the knit, the volume of which is capable of receiving the melted and flattened barbs of the barb-free zone formed by application, with pressure, of the heated anvil as described above. Thus, the melted and flattened barbs are incorporated into the base structure of the knit formed from the first yarns. Furthermore, such embodiments make it possible to produce openings that are large enough for the knit to retain an openwork structure, even in the barb-free zones, i.e. the zones where the barbs have been flattened, for good cell recolonization of the knit once the latter is implanted.

In one embodiment, said barbs protrude outwards from said first face over a length ranging from 1 to 2 mm, preferably over a length of around 1.5 mm. Such a length of the barbs enables both a good fastening of the barbs to the biological tissues and an optimized manufacturing process. Such a length of the barbs makes it possible in particular to preserve the integrity of the yarns forming the knit during the formation of the barbs by melting of the loops as described in WO01/81667.

The advantages of the present invention will emerge from the following examples and from the figures in which:

FIGS. 1A to 1C show the respective charts of three guide bars used for obtaining a knit according to the invention, FIG. 2 is a partial top view of a knit according to the invention, FIG. 3 is a cross section of the knit from FIG. 2.

EXAMPLE 1

The following knit according to the invention is produced on a warp knitting machine:

Knit A: having the following chart according to the ISO 11676 standard:
bar B1: 1.0/0.1/
bar B2: 1.0/5.5/1.0/3.3/
bar B3: 2.1/5.5/3.4/0.0/

The respective charts for bars B1, B2 and B3 are illustrated in FIGS. 1A to 1C.

Alternatively, the chart of bar B2 could be replaced by the following: 1.0/7.7/6.6/7.7/

Bar B1 and bar B2 are each threaded continuously 1 full, 1 empty, over the width of the knitting machine with a monofilament yarn made of polyethylene terephthalate (PET) having a diameter of 0.08 mm, commercially available from the company SIDER ARC. The melting point of this monofilament yarn made of polyethylene terephthalate (PET) is 258° C.

Bar B3, which will give rise to the barbs, is threaded continuously 1 full, 3 empty, over the width of the knitting machine with a heat-fusible monofilament yarn made of polylactic acid having a diameter of 0.15 mm. The melting point of this monofilament yarn made of polylactic acid is 185° C.

The knitting according to the chart above leads to the formation of loops that protrude outwards from one face of the knit by the heat-fusible monofilament made of polylactic acid.

After knitting, the loops are cut by melting as described in WO01/81667 in order to obtain barbs. The knit 1 obtained is shown in FIG. 2: the first face, namely the top face 2 in FIG. 2, is provided with barbs 3 that protrude outwards with respect to this face 2. Generally the barbs 3 have the shape of a shaft having the diameter of the yarn used for their formation, surmounted by a head having a diameter greater than that of the shaft. The barbs 3 protrude outwards from the first face 2 over a length of around 1.5 mm. Such a length of the barbs 3 enables a good fastening of the barbs in the biological tissues during the implantation of the knit 1 or of a prosthesis comprising this knit 1. Furthermore, such a length of the barbs 3 makes it possible in particular to preserve the integrity of the monofilament yarns made of polyethylene terephthalate (PET) forming the knit 1 during the formation of the barbs by melting the loops as described in WO01/81667, the hotplate used for melting the loops thus being kept at a sufficient distance from the monofilament yarns made of polyethylene terephthalate (PET) that form the ground structure of the knit 1.

Once the barbs 3 are formed, an anvil 4 heated to 185° C. is applied to a given zone of the knit 1, as shown in FIG. 2. The anvil 4 is brought into contact with the barbs 3 of the given zone with a pressure of around 100 N: the barbs 3 melt and are flattened within openings of the base knit formed by the first yarns made of polyethylene terephthalate (PET), and a knit 1 is obtained that comprises a barb-free zone 5, and a zone 7 provided with barbs 3 as shown in FIG. 3. Indeed, in zone 5, the flattened and melted barbs 6 are incorporated within the base knit formed by the first monofilament yarns made of polyethylene terephthalate (PET) and they no longer protrude outwards from the first face 2 of the knit 1. Thus, at the barb-free zone 5, the first face 2 has a relatively smooth and non-traumatizing appearance. Zone 5 has the shape of the anvil 4. For example, it may have the shape of a disc, a rectangle or an oval: this shape may adopt any possible shape, in particular a shape corresponding to the surface of the fragile organ or organs opposite which this zone 5 of the knit 1 will be placed after implantation of the knit 1.

Furthermore, considering the fact that the first yarns made of polyethylene terephthalate (PET) have a melting point above 185° C., the latter were not damaged by the application of the heated anvil 4, and the base structure of the knit 1 was not modified and retained its integrity.

Such a knit 1 has the same mechanical properties over the whole of its surface. In particular, it has the same mechanical properties as the knit that would be obtained if the barbs of zone 5 were not melted and flattened.

Finally, the chart defined above for the knitting of the knit 1 makes it possible to obtain openings in the knit 1 that are large enough to allow the knit 1 to retain a good aptitude for cell recolonization, even at the zone 5 free of barbs that protrude outwards, in which the barbs 6 are flattened within these same openings. Thus, the flattened barbs 6 do not block the openings of the knit 1, which retains its aptitude for promoting cell recolonization.

The knit 1 from the present example may be used as it is or in combination with other textiles in order to form reinforcing prostheses, for example abdominal wall reinforcing prostheses.

The invention claimed is:

1. An openwork prosthetic knit comprising a single piece based on at least a first yarn made of biocompatible polymer material that defines a first face and a second face that are opposite one another and on a second biocompatible yarn that generates barbs, wherein said first face comprises at least a first zone provided with barbs that protrude outwards from at least said first face and at least a second zone provided with barbs that do not protrude outward from said first face and are incorporated within said knit.

2. The openwork prosthetic knit according to claim 1, wherein said first face comprises several of said first zones provided with said barbs that protrude outwards from at least said first face, and several of said second zones provided with barbs that do not protrude outward from said first face and are incorporated within said knit.

3. The openwork prosthetic knit according to claim 1, wherein said second yarn is a heat-fusible monofilament yarn.

4. The openwork prosthetic knit according to claim 3, wherein said first yarns have a melting point strictly above that of said second yarn.

5. The openwork prosthetic knit according to claim 3, wherein said second yarn is a monofilament yarn made of polylactic acid and said first yarns are monofilament yarns made of polyethylene terephthalate (PET).

6. The openwork prosthetic knit according to claim 1, wherein the barbs that do not protrude outward from said first face and are incorporated within said knit comprise flattened barbs.

7. The openwork prosthetic knit according to claim 1, wherein the barbs that do not protrude outward from said first face and are incorporated within said knit comprise melted barbs.

8. The openwork prosthetic knit according to claim 1, wherein the barbs that do not protrude outward from said first face and are incorporated within said knit comprise flattened and melted barbs.

9. The openwork prosthetic knit according to claim 1, wherein the barbs that do not protrude outward from said first face and are incorporated within said knit do not block openings of the first or second face of the knit thereby retaining an aptitude for cell recolonization.

10. A process for manufacturing a knit, comprising the following steps:
    a) manufacturing an arrangement of at least one first yarn of biocompatible polymer material that defines a first face and a second face that are opposite one another for said knit and of at least one second yarn comprising a biocompatible heat-fusible monofilament yarn, that forms small loops that protrude outwards from said first face, by knitting-on a warp or Raschel knitting machine of said first yarn(s) and second yarns using at least three guide bars, said first yarn(s) being threaded, continuously on two of said three guide bars, and said second yarn being threaded continuously on the third guide bar,
    b) cutting, by melting, of said loops, each loop generating two barbs that protrude outward from said first face,
    c) melting and flattening said barbs that protrude outward from said first face over one or more given zone(s) of the first face by application, with pressure, to said zone(s) of an anvil heated to a melting point of said barbs to provide melted and flattened barbs that do not protrude outward from said first face and are incorporated within said knit.

11. The process according to claim 10, wherein, said first yarns comprise monofilament yarns made of polyethylene terephthalate (PET).

12. The process according to claim 11, wherein said second yarn comprises a monofilament yarn made of polylactic acid.

13. The process according to claim 12, wherein the melting temperature of the polyethylene terephthalate is above 185° C.

14. The process according to claim 13, wherein the melting temperature of the polylactic acid is around 185° C.

15. The process according to claim 14, wherein the pressure with which the anvil is applied is around 100 N.

16. The process according to claim 15, wherein a temperature of said anvil is around 185° C.

17. The process according to claim 12, wherein the melting temperature of the polyethylene terephthalate is around 258° C.

18. The process according to claim 10, wherein the knitting of said first and second yarns is according to the following charts:
    for said first yarns, threaded on two guide bars B1 and B2, according to the ISO 11676 standard:
    bar B1: 1.0/0.1/
    bar B2: 1.0/5.5/1.0/3.3/ or 1.0/7.716.6/7.7/
    for said second yarn, threaded on the third guide bar B3, according to the ISO 11676 standard:
    bar B3: 2.1/5.5/3.4/0.0/.

19. The process according to claim 10, wherein the knit comprises first zones that have fastening capabilities and second zones that are smooth and non-traumatizing.

20. A prosthetic implant for treating hernias by temporarily or permanently filling a tissue defect comprising at least one knit made from the process according to claim 10.

* * * * *